United States Patent
Choi et al.

(10) Patent No.: US 11,407,761 B2
(45) Date of Patent: Aug. 9, 2022

(54) DERIVATIVE OF β-APOPICROPODOPHYLLIN AND METHOD OF PREPARING THEREOF

(71) Applicant: J&C Sciences, Daejeon (KR)

(72) Inventors: Jong-Ryoo Choi, Daejeon (KR); In-Young Choi, Daejeon (KR); So-Yeon Nam, Daejeon (KR); Se Hee Hyun, Daejeon (KR)

(73) Assignee: J&C SCIENCES, Daejeon (KR)

( * ) Notice: Subject to any disclaimer, the term of this patent is extended or adjusted under 35 U.S.C. 154(b) by 190 days.

(21) Appl. No.: 16/991,190

(22) Filed: Aug. 12, 2020

(65) Prior Publication Data

US 2021/0347783 A1    Nov. 11, 2021

(30) Foreign Application Priority Data

May 11, 2020    (KR) .................. 10-2020-0055887

(51) Int. Cl.
*C07D 493/04*   (2006.01)
(52) U.S. Cl.
CPC ................... *C07D 493/04* (2013.01)
(58) Field of Classification Search
None
See application file for complete search history.

(56) References Cited

FOREIGN PATENT DOCUMENTS

| | | |
|---|---|---|
| EP | 0196618 | 10/1986 |
| GB | 2207674 | 9/1991 |
| KR | 20040007743 | 1/2004 |
| KR | 10-2090554 | 10/2019 |
| WO | 2002040489 | 5/2002 |
| WO | 2002102804 | 12/2002 |
| WO | 2012076942 | 6/2012 |

OTHER PUBLICATIONS

Chemical Abstracts of 58:39905 from Polonsky et al, Bulletin de la Societe Chimique de France, pp. 1722-1726 (Year: 1962).*
KIPO, Office Action of KR 10-2020-0055887 dated Jul. 7, 2021.
Hitoshi Saito et al., "Studies Lignan Lactone Antitumor Agents. IV. Synthesis of Glycosidic Lignan Variants Related to alpha-Peltatin", Bulletin of the Chemical Society of Japan, 61, 1259-1263 (1988).
Lee S. Thurston et al., "Antitumor Agents. 78. Inhibition of Human DNA Topoisomerase II by Podophyllotoxin and alpha-Peltatin Analogues" Journal of Medicinal Chemistry, 1986, vol. 29, No. 8, 1547-1550, 1986.
Alex P. Mathe et al. "Reduction of Some Grignard Reagent-Carbon Dioxide Adducts to Primary Alcohols by Lithium Aluminum Hydride", Journal of the american chemical society 1954 vol. 76 1182-1185, Feb. 1954.
Ju Yeon Kim et al., "A novel anti-cancer role of β-apopicropodophyllin against non-small cell lung cancer cells", Toxicology and Applied Pharmacology, 2018, 357, 39-49, Aug. 2018.

* cited by examiner

*Primary Examiner* — Zinna Northington Davis
(74) *Attorney, Agent, or Firm* — Lex IP Meister, PLLC

(57) ABSTRACT

Provided are a novel derivative of β-apopicropodophyllin and a method of preparing the same, and more particularly, a compound represented by Formula 1 below, which is a novel derivative of β-apopicropodophyllin derived from podophyllotoxin, which is an anticancer agent, a method of preparing the same, and a composition for treating cancer, which includes the compound.

[Formula 1]

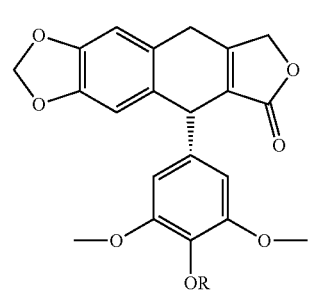

In Formula 1, R is a $C_2$ to $C_{10}$ alkyl group, a $C_2$ to $C_{10}$ alkyl group containing an allyl- or alkyne, a —$[CH_2]_n$—$C_3$ to $C_8$ cycloalkyl group, a substituted or unsubstituted —$[CH_2]_n$-phenyl group, a substituted or unsubstituted —$[CH_2]_n$—$C_5$ to $C_6$ heteroaromatic group, a —$C(=O)$—$C_1$ to $C_8$ alkyl group, a substituted or unsubstituted —$C(=O)$—$[CH_2]_n$-phenyl group, or a substituted or unsubstituted —$C(=O)$—$[CH_2]_n$—$C_5$ to $C_6$ heteroaromatic group, wherein n is an integer of 0 to 6.

3 Claims, No Drawings

DERIVATIVE OF β-APOPICROPODOPHYLLIN AND METHOD OF PREPARING THEREOF

TECHNICAL FIELD

The present invention relates to a novel derivative of β-apopicropodophyllin and a method of preparing the same, and more particularly, a compound represented by Formula 1 below, which is a novel derivative of β-apopicropodophyllin derived from podophyllotoxin, which is an anticancer agent, a method of preparing the same, and a composition for treating cancer, which includes the compound.

[Formula 1]

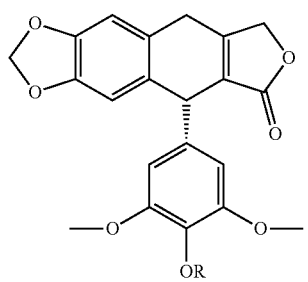

In Formula 1, R is a $C_2$ to $C_{10}$ alkyl group, a $C_2$ to $C_{10}$ alkyl group containing an allyl- or alkyne, a —$[CH_2]_n$—$C_3$ to $C_8$ cycloalkyl group, a substituted or unsubstituted —$[CH_2]_n$-phenyl group, a substituted or unsubstituted —$[CH_2]_n$—$C_5$ to $C_6$ heteroaromatic group, a —C(=O)—$C_1$ to $C_8$ alkyl group, a substituted or unsubstituted —C(=O)—$[CH_2]_n$-phenyl group, or a substituted or unsubstituted —C(=O)—$[CH_2]_n$—$C_5$ to $C_6$ heteroaromatic group, wherein n is an integer of 0 to 6.

BACKGROUND ART

Podophyllotoxins has been used as therapeutics for more than 1,000 years. In the 1960s, Sandoz Limited synthesized derivatives of podophyllotoxin, below Formula A. Semi-synthetic derivatives of podophyllotoxin, etoposide and teniposide were obtained in 1966 and 1967, respectively. In 1987, etoposide got US FDA approval as an antineoplastic drug. Teniposide got US FDA approval for clinical use for several types of cancer, lung, leukemia and so on in 1993. Both two anti-cancer agents have been used single, combination therapy with other anti-cancer agents.

[Formula A]

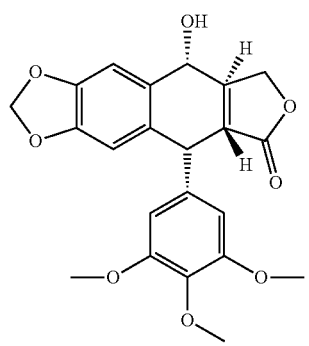

Mode of action of podophyllotoxin, etoposide, teniposide and other podophyllotoxin derivatives as an anticancer agent had been published DNA topoisomerase II inhibition (J. C. Wang, J. Biol. Chem., 1991, 266(11), 6659-62). Although etoposide and teniposide have been showed good clinical effect in cancer patients, they have limitation for long term treatment as toxicity. The discovery and developing research for new drug to overcome the shortcoming has been continued.

Bristol-Myers Squibb Co. in US and Microbial Chemistry Research Foundation in Japan issued patent GB 2,207,674 A (Feb. 8, 1989) and EP 0,196,618 A1 (Oct. 8, 1986), respectively. And Adla Mallareddy, et al. in India suggested 4-Aza-2,3-didehydropotophyllotoxin derivatives and anti-cancer effect WO 2012/076942 A1 (Jun. 14, 2012) and also Kim, Song-Bae in S. Korea did 4'-demethy-4'-O-substituted-1-deoxypodophyllotoxin derivatives and anticancer effect (WO 2002/040489 A1 (May 5, 2002).

β-Apopicropodophyllin of below Formula B and 4'-demethyl-β-apopicropodophyllin of below Formula C were obtained and identified by halogenation and followed by pyrolysis from podophyllotoxin, and demethylation of β-apopicropodophyllin, respectively (Journal of the American Chemical Society, 1954, 76, 1182-1185).

[Formula B]

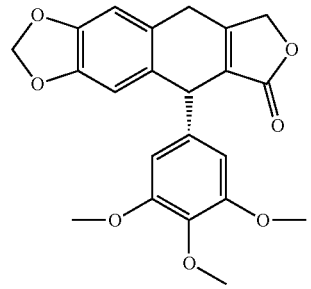

[Formula C]

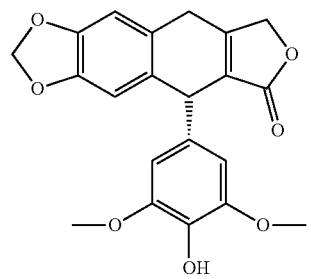

Anti-cancer effect of β-apopicropodophyllin (Formula B) in detail was published in 2018 [Toxicology and Applied Pharmacology, 2018, 357, 39-49 and patent KP 10-2090554 B1 (Mar. 12, 2020)]. While, in 1986, Anticancer effect and inhibition of human DNA-topoisomerase II were not reported in detail (Journal of Medicinal Chemistry, 1986, 29, 1547-1550).

PRIOR ART DOCUMENTS

Patent Document

EP 0,196,618 A1 (Oct. 8, 1986)
GB 2,207,674 A1 (Feb. 8, 1989)
WO 2002/040489 A1 (May 23, 2002)
WO 2012/76942 A1 (Jun. 14, 2012)
KP 10-2090554 B1 (Mar. 12, 2020)

Non-Patent Document

Journal of the American Chemical Society, 1954, 76, 1182-1185
Journal of Medicinal Chemistry, 1986, 29, 1547-1550
Toxicology and Applied Pharmacology, 2018, 357, 39-49

DISCLOSURE

Technical Problem

As described above, many derivatives of podophyllotoxin have been studied for a new anticancer agent, but most of them were stopped the development stage due to efficacy and/or side effect. Thus, the present invention was extensively studied O-apopicropodophyllin derivatives to discover a new chemical entity, which is more potent and less side effect as compared with previous studies. Therefore, this present invention discloses a β-apopicropodophyllin derivative, stereoisomer, useful of as an anticancer agent, pharmaceutically acceptable salt, and a preparation method of the derivative.

Technical Solution

The compound of Formula 1 according to the present invention is a β-apopicropodophyllin derivative accomplished by modification of 4'-position of β-apopicropodophyllin:

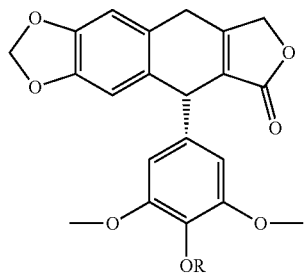

[Formula 1]

In Formula 1, R is a $C_2$ to $C_{10}$ alkyl group, a $C_2$ to $C_{10}$ alkyl group containing an allyl- or alkyne, a —[CH$_2$]$_n$—$C_3$ to $C_8$ cycloalkyl group, a substituted or unsubstituted —[CH$_2$]$_n$-phenyl group, a substituted or unsubstituted —[CH$_2$]$_n$—$C_5$ to $C_6$ heteroaromatic group, a —C(=O)—$C_1$ to $C_8$ alkyl group, a substituted or unsubstituted —C(=O)—[CH$_2$]$_n$-phenyl group, or a substituted or unsubstituted —C(=O)—[CH$_2$]$_n$—$C_5$ to $C_6$ heteroaromatic group, wherein n is an integer of 0 to 6.

A method of preparing a compound of Formula 1 comprises a step obtaining a target compound by reacting 4'-demethyl-β-apopicropodophyllin[(5S)-5-(4-hydroxy-3,5-dimethoxy-phenyl)-5,9-dihydro-8H-furo[3',4':6,7]naphtho[2,3-d][1,3]dioxol-6-one] with a chemical (R-L) in which a leaving group (L) binds to a substituent (R) introduced to the 4'-position of 4'-demethyl-β-apopicropodophyllin in the presence of an organic or inorganic base.

Advantageous Effects

The compound of Formula 1 of the present invention exhibits a potent anticancer effect in selected human cancer cell lines i.e., lung, colon, and blood cancer cell line.

Accordingly, the compound of Formula 1 can be usefully used as a new anticancer agent that can replace the conventional podophyllotoxin derivatives.

Modes of the Invention

Preferred compounds among the Formula 1 compounds according to the present invention are shown in the following [Table 1].

TABLE 1

| No. | chemical structure |
|---|---|
| 1-1 | 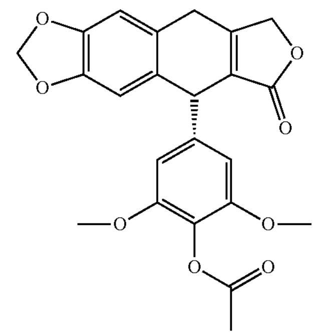 |
| 1-2 | 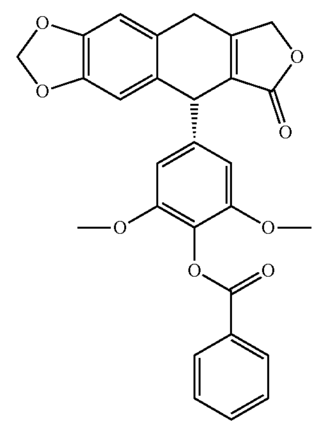 |
| 1-3 | 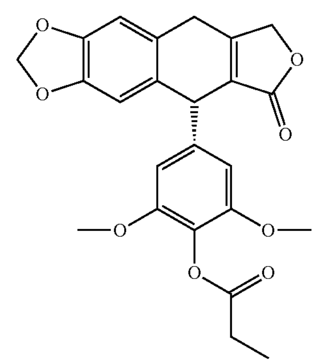 |

TABLE 1-continued
| No. | chemical structure |
|---|---|
| 1-4 | 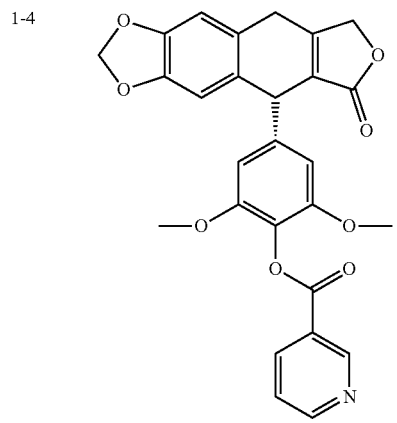 |
| 1-5 | 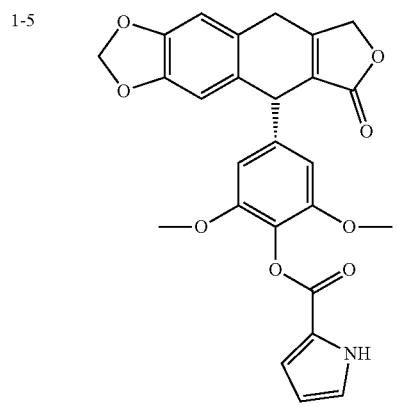 |
| 1-6 | 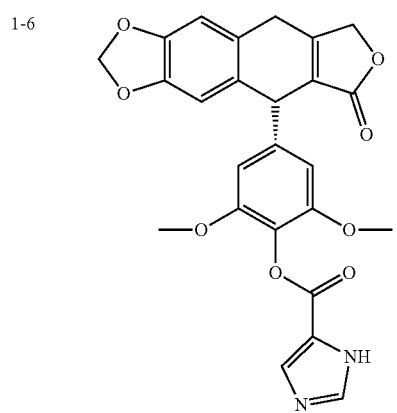 |
TABLE 1-continued
| No. | chemical structure |
|---|---|
| 1-7 | 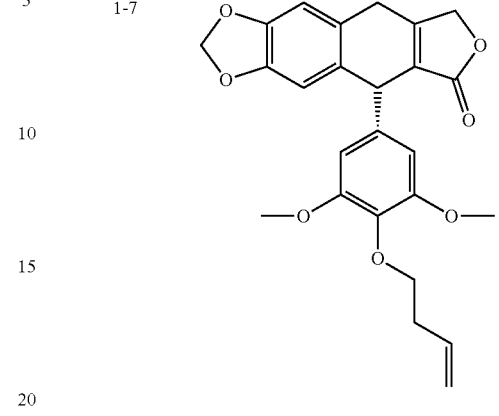 |
| 1-8 | 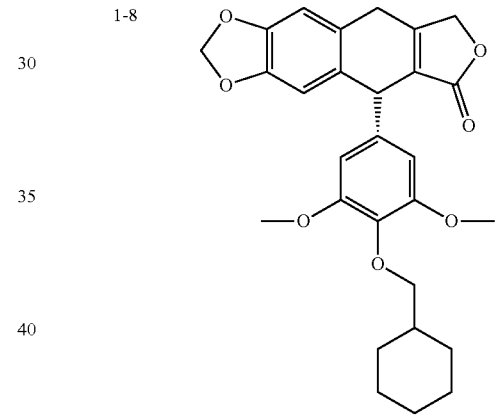 |
| 1-9 | 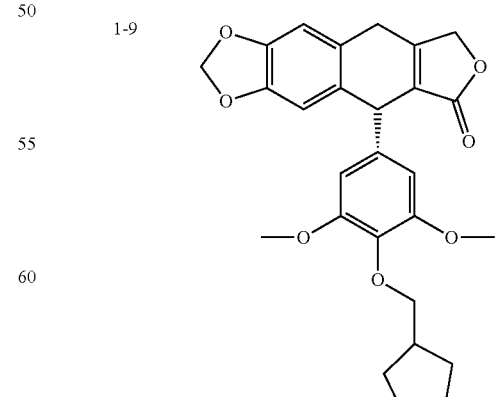 |

TABLE 1-continued

| No. | chemical structure |
|---|---|
| 1-10 | 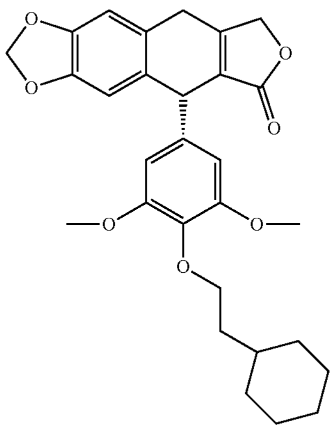 |
| 1-11 | 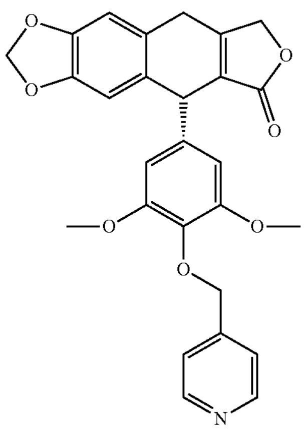 |
| 1-12 | 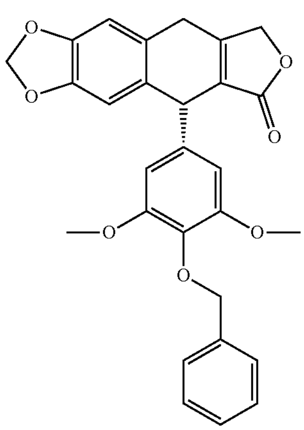 |
| 1-13 | |
| 1-14 | |
| 1-15 | |

Following [Table 2] shows chemical names of the 1-1 to 1-15 compound illustrated in the above [Table 1].

TABLE 2

| No. | chemical name |
|---|---|
| 1-1 | Acetic acid (5S)-2,6-dimethoxy-4-(6-oxo-5,6,8,9-tetrahydrofuro[3',4':6,7]naphtho[2,3-d][1,3]dioxol-5-yl)-phenyl ester |
| 1-2 | Benzoic acid (5S)-2,6-dimethoxy-4-(6-oxo-5,6,8,9-tetrahydrofuro[3',4':6,7]naphtho[2,3-d][1,3]dioxol-5-yl)-phenyl ester |
| 1-3 | Propionic acid (5S)-2,6-dimethoxy-4-(6-oxo-5,6,8,9-tetrahydrofuro[3',4':6,7]naphtho[2,3-d][1,3]dioxol-5-yl)-phenyl ester |
| 1-4 | Nicotinic acid (5S)-2,6-dimethoxy-4-(6-oxo-5,6,8,9-tetrahydrofuro[3',4':6,7]naphtho[2,3-d][1,3]dioxol-5-yl)-phenyl ester |
| 1-5 | 1H-Pyrrole-2-carboxylic acid (5S)-2,6-dimethoxy-4-(6-oxo-5,6,8,9-tetrahydrofuro[3',4':6,7]naphtho[2,3-d][1,3]dioxol-5-yl)-phenyl ester |
| 1-6 | 3H-Imidazol-4-carboxylic acid (5S)-2,6-dimethoxy-4-(6-oxo-5,6,8,9-tetrahydrofuro[3',4':6,7]naphtho[2,3-d][1,3]dioxol-5-yl)-phenyl ester |
| 1-7 | (5S)-5-(4-But-3-enyloxy-3,5-dimethoxy-phenyl)-5,9-dihydro-8H-furo[3',4':6,7]naphtho[2,3-d][1,3]dioxol-6-one |
| 1-8 | (5S)-5-(4-Cyclohexylmethoxy-3,5-dimethoxy-phenyl)-5,9-dihydro-8H-furo[3',4':6,7]naphtho[2,3-d][1,3]dioxol-6-one |
| 1-9 | (5S)-5-(4-Cyclopentylmethoxy-3,5-dimethoxy-phenyl)-5,9-dihydro-8H-furo[3',4':6,7]naphtho[2,3-d][1,3]dioxol-6-one |
| 1-10 | (5S)-5-[4-(2-Cyclohexyl-ethoxy)-3,5-dimethoxy-phenyl]-5,9-dihydro-8H-furo[3',4':6,7]naphtho[2,3-d][1,3]dioxol-6-one |
| 1-11 | (5S)-5-[3,5-Dimethoxy-4-(pyridin-4-ylmethoxy)-phenyl]-5,9-dihydro-8H-furo[3',4':6,7]naphtho[2,3-d][1,3]dioxol-6-one |
| 1-12 | (5S)-5-(4-Benzyloxy-3,5-dimethoxy-phenyl)-5,9-dihydro-8H-furo[3',4':6,7]naphtho[2,3-d][1,3]dioxol-6-one |
| 1-13 | (5S)-5-[3,5-Dimethoxy-4-(4-trifluoromethyl-benzyloxy)-phenyl]-5,9-dihydro-8H-furo[3',4':6,7]naphtho[2,3-d][1,3]dioxol-6-one |
| 1-14 | (5S)-5-[3,5-Dimethoxy-4-(4-methyl-benzyloxy)-phenyl]-5,9-dihydro-8H-furo[3',4':6,7]naphtho[2,3-d][1,3]dioxol-6-one |
| 1-15 | (5S)-5-[3,5-Dimethoxy-4-(4-fluorobenzyloxy)-phenyl]-5,9-dihydro-8H-furo[3',4':6,7]naphtho[2,3-d][1,3]dioxol-6-one |

The compound of the Formula 1 may be prepared through following [Reaction scheme 1] and [Reaction scheme 2].

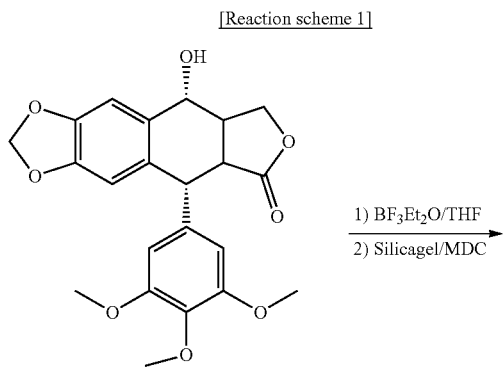

[Reaction scheme 1]

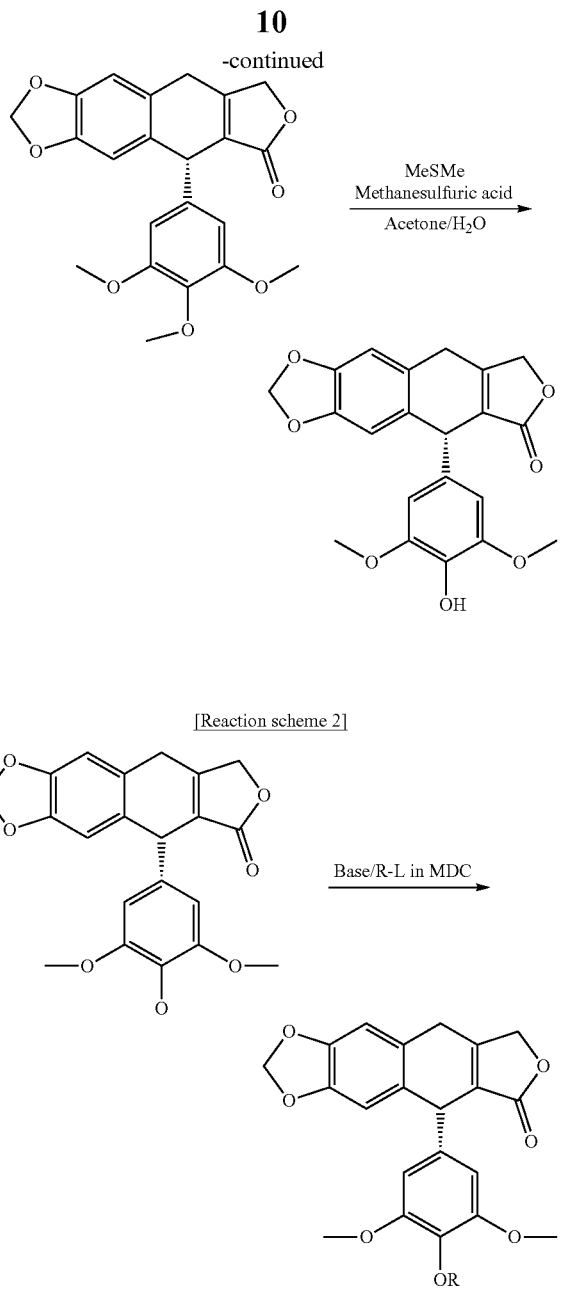

As described reaction scheme 1 and 2, the process for preparing of the Formula 1 compound can be classified 3 steps, S1, S2 and S3. S1 step is to convert podophyllotoxin formula A to β-apopicropodophyllin formula B, S2 step is β-apopicropodophyllin to 4'-demethyl-β-apopicropodophyllin as described in reaction scheme 1, and S3 is 4'-demethyl-β-apopicropodophyllin to the present invention compound described in Formula 1 as described in reaction scheme 2.

Reaction scheme 1 depicts the S1 step and S2 step. S1 step is explained a dehydration of 9-OH of podophyllotoxin and a forming double bond migration to give β-apopicropodophyllin by treatment with boron trifluoride etherate (BF$_3$Et$_2$O) in tetrahydrofuran (THF) followed by silica gel treatment in dichloromethan (MDC). And S2 step is explained 4'-demethylation of β-apopicropodophyllin to give 4'-demethyl-β-apopicropodophyllin by treatment with dimethylsulfide (MeSMe) in mixed solvent of acetone and methanol.

Reaction scheme 2 depicts S3 step to explain a preparation of the present invention compound described in Formula 1 from 4'-demethyl-β-apopicropodophyllin obtained in step 1 and 2. The formed 4'-demethyl-β-apopicropodophyllin is treated with a reagent (R-L) that has a covalent bond between a introducing group (R) and a leaving group (L) in the present of organic or inorganic base to give the present invention compound described in Formula 1. In which, R is defined as previously described in Formula 1 and leaving group L is halogen (F, Cl, Br, I), toluensulfonate (OTs), methansulfonate (OMs) or an equivalent leaving group. A possible organic or inorganic base for S3 step is NaH, LDA (lithium diisopropylamine), TEA (triethylamine), Pyridine, DIPEA (diisopropylethylamine), $K_2CO_3$, or $NaHCO_3$.

Since the compound of Formula 1, according to this invention may have one or more asymmetric carbon atoms in the chemical structure depending on the type of substituents, it can be present in the individual enantiomers, diastereoisomers, regioisomers, E or Z isomers. Therefore, this present invention includes all of these isomers and mixtures. Also, the compound of Formula 1, according to this invention includes pharmaceutically acceptable salt, such as organic acid salt, phosphoric acid, hydrochloric acid, sulfuric acid, methanesulfonic acid, etc.

For Human or animal, the compound of Formula 1 of the present invention can be effectively used as an anti-cancer agent, alone or combination with other anti-cancer agents such as a cisplatin family or a check point inhibitor anti-cancer agent such as PD-1 or PD-L1 inhibitor. Therefore, it is another object of the present invention to provide a composition for the treatment of cancer, which comprises as an active ingredient the compound of the present invention Formula 1, pharmaceutically acceptable salt, hydrate, solvate or isomer thereof together with the pharmaceutically acceptable carrier. The compound of the present invention can be administrated in the form of injection or oral preparation.

When the active compound according to the present invention is used for clinical purpose, it is preferably administrated in an amount ranging generally from 0.5 mg to 50 mg, preferably from 2 mg to 30 mg per kg of body weight a day. The total daily dosage may be administrated in once or over several times. However, the specific administration dosage for the patient can be varied with the specific compound used, body weight, sex or hygienic condition of the subject patient, diet, time or method of administration, excretion rate mixing ration of the agent, severity of the disease to be treated, etc.

The present invention will be more specifically explained in the following Examples and Experiments. However, these Examples and Experiments are intended to illustrate the present invention but not in any manner to limit the scope of the present invention.

[Preparation 1]

Synthesis of (5S)-5-(3,4,5-Trimethoxy-phenyl)-5,9-dihydro-8H-furo[3',4':6,7]naphtho [2,3-d][1,3]dioxol-6-one (Formula B)

To a stirred solution of podophyllotoxin (20 g, 48.2 mmol) in tetrahydrofuran (260 mL) was added boron trifluoride methyl etherate (137 g, 96.5 mmol) at room temperature. After the reaction mixture was stirred for 4 hrs, tetrahydrofuran was concentrated in vacuo. The mixture was made acidic (pH 4-6) with the addition of saturated aqueous $NaHCO_3$ at below 10° C., and extracted with dichloromethane (400 mL). The organic layer was dried over $MgSO_4$ and concentrated in vacuo. The residue was stirred with silica gel (100 g) in dichloromethane (200 mL) for 4 hrs, filtered and concentrated in vacuo. The concentrate was crystallized from tetrahydrofuran (100 mL) to afford 14 g (73%) of the desired product as a white solid.

$^1$H NMR (CDCl$_3$) δ (ppm): 6.72 (s, 1H), 6.63 (s, 1H), 6.37 (s, 1H), 5.95 (dd, J=6.1, 1.2 Hz, 2H), 4.89 (d, J=17.3 Hz, 1H), 4.86-4.79 (m, 2H), 3.85 (dd, J=22.1, 4.0 Hz, 1H), 3.79 (s, 3H), 3.78 (s, 6H), 3.65 (dd, J=22.2, 3.9 Hz, 1H)

[Preparation 2]

Synthesis of (5S)-5-(4-Hydroxy-3,5-dimethoxy-phenyl)-5,9-dihydro-8H-furo[3',4':6,7]naphtho[2,3-d][1,3]dioxol-6-one (Formula C)

To a stirred solution of β-apopicropodophyllin (10 g, 25.2 mmol) in acetone (4.2 mL) and water (0.8 mL) was added dimethyl sulfide (9.4 g, 151.2 mmol) and methane sulfonic acid (48 g, 504 mmol) at room temperature. The reaction mixture was stirred for 2 hrs, added ice water to form a solid. The solid was collected by filtration and was recrystallized from tetrahydrofuran (70 mL) to afford 5.2 g (54%) of the desired product as a white solid.

$^1$H NMR (DMSO) δ (ppm): 8.18 (s, 1H), 6.83 (s, 1H), 6.75 (s, 1H), 5.96 (s, 1H), 5.90 (s, 1H), 5.05 (d, J=17.3 Hz, 1H), 4.94 (d, J=17.1 Hz, 1H), 4.66 (s, 1H), 3.93 (dd, J=22.9, 3.3 Hz, 1H), 3.70 (d, J=3.3 Hz, 1H), 3.66 (s, 1H)

EXAMPLE 1

Synthesis of acetic acid (5S)-2,6-dimethoxy-4-(6-oxo-5,6,8,9-tetrahydro-furo[3',4':6,7]naphtho[2,3-d][1,3]dioxol-5-yl)-phenyl ester (1-1 Compound)

To a stirred solution of 4'-demethyl-β-apopicropodophyllin (7 g, 18.3 mmol), 4-(dimethylamino)pyridine (0.22 g, 1.83 mmol) and triethylamine (4.45 g, 43.9 mmol) in dichloromethane (70 mL) was added dropwise acetyl chloride (1.72 g, 21.9 mmol) at below 0° C. After the reaction mixture was stirred for 2 hrs, the reaction mixture was washed twice with water (270 mL), dried over $MgSO_4$ and concentrated in vacuo. The concentrate was purified by column chromatography on silica gel (ethyl acetate/n-hexane:1/4) to afford 4.5 g (58%) of the desired product.

$^1$H NMR (CDCl$_3$) δ (ppm): 6.73 (s, 1H), 6.65 (s, 1H), 6.42 (s, 2H), 6.02-5.94 (m, 2H), 4.87 (d, J=6.0 Hz, 2H), 4.82 (d, J=2.0 Hz, 1H), 3.78 (d, J=5.2 Hz, 1H), 3.73 (s, 6H), 3.66 (d, J=3.6 Hz, 1H), 2.30 (s, 3H)

EXAMPLE 2

Synthesis of benzoic acid (5S)-2,6-dimethoxy-4-(6-oxo-5,6,8,9-tetrahydro-furo[3',4':6,7]naphtho[2,3-d][1,3]dioxol-5-yl)-phenyl ester (1-2 Compound)

To a stirred solution of 4'-demethyl-β-apopicropodophyllin (9 g, 23.5 mmol), 4-(dimethylamino)pyridine (0.29 g, 2.35 mmol), and triethylamine (5.72 g, 56.5 mmol) in dichloromethane (90 mL) was added dropwise benzoyl chloride (3.97 g, 28.25 mmol) at below 0° C. After the reaction mixture was stirred for 2 hrs, the reaction mixture was washed twice with water (90 mL), dried over $MgSO_4$ and concentrated in vacuo. The concentrate was purified by column chromatography on silica gel (ethyl acetate/n-hexane:1/2) to afford 9.5 g (83%) of the desired product.

$^1$H NMR (CDCl$_3$) δ (ppm): 8.25-8.15 (m, 2H), 7.65-7.55 (m, 1H), 7.51-7.48 (m, 2H), 6.74 (s, 1H), 6.67 (s, 1H), 6.46

(s, 2H), 5.97 (dd, J=4.6, 1.3 Hz, 2H), 4.95-4.87 (m, 2H), 4.84 (s, 1H), 3.90-3.62 (m, 2H), 3.72 (s, 6H) [Example 3]

Synthesis of (5S)-5-(4-benzyloxy-3,5-dimethoxy-phenyl)-5,9-dihydro-8H-furo[3',4':6,7]naphtho[2,3-d][1,3]dioxol-6-one (Compound 1-12)

To a stirred solution of 4'-demethyl-β-apopicropodophyllin (10 g, 26.2 mmol) in anhydrous N,N-dimethylformamide (100 mL) was added portionwise sodium hydride (1.26 g, 60%, 31.4 mmol) at below 0° C. After the mixture was stirred at same temperature for 1 hr, benzyl bromide (6.7 g, 39.2 mmol) was added dropwise to the mixture. The reaction mixture was stirred at room temperature overnight, quenched with water (300 mL) and extracted with ethyl acetate (2×100 mL). The combined organic layer was washed twice with water (50 mL), dried over MgSO$_4$ and concentrated in vacuo. The concentrate was purified by column chromatography on silica gel (ethyl acetate/n-hexane:1/4) to afford 7.7 g (62%) of the desired product.

$^1$H NMR (CDCl$_3$) δ (ppm): 7.46 (d, J=7.2 Hz, 2H), 7.40-7.28 (m, 3H), 6.70 (s, 1H), 6.62 (s, 1H), 6.37 (s, 2H), 5.97 (dd, J=3.2, 1.2 Hz, 2H), 4.93 (s, 2H), 4.88-4.81 (m, 2H), 4.78 (d, J=7.4 Hz, 1H), 3.79 (d, J=2.1 Hz, 1H), 3.80-3.67 (m, 2H), 3.75 (s, 6H)

EXAMPLE 4

Synthesis of (5S)-5-(4-cyclohexylmethoxy-3,5-dimethoxy-phenyl)-5,9-dihydro-8H-furo [3',4':6,7]naphtho[2,3-d][1,3]dioxol-6-one (compound 1-8)

To a stirred solution of 4'-demethyl-β-apopicropodophyllin (200 mg, 0.52 mmol) in anhydrous N,N-dimethylformamide (1 mL) was added sodium hydride (27 mg, 60%, 0.67 mmol) at below 0° C. After the mixture was stirred at same temperature for 1 hr, cyclohexylmethyl trifluorosulfonate (170 mg, 0.68 mmol) (reference of preparation, Journal of medicinal chemistry, 2015, vol. 58, pp 6151-6178) was added dropwise to the mixture. The reaction mixture was stirred for 1 hr, quenched with water (10 mL) and extracted with ethyl acetate (2×10 mL). The combined organic layer was washed twice with water (5 mL), dried over MgSO$_4$ and concentrated in vacuo. The concentrate was purified by column chromatography on silica gel (ethyl acetate/n-hexane:1/3) to afford 106 mg (43%) of the desired product.

NMR(CDCl$_3$) δ (ppm): 6.71 (s, 1H), 6.63 (s, 1H), 6.36 (s, 2H), 5.95 (d, J=1.9 Hz, 2H), 4.82 (s, 1H), 4.80-4.70 (m, 2H), 3.85 (dd, J=15.1, 7.1 Hz, 1H), 3.75 (s, 6H), 3.68 (d, J=6.6 Hz, 2H), 3-66-3.59 (m, 1H), 1.89 (d, J=13.0 Hz, 2H), 1.80-1.64 (m, 4H), 1.30-0.90 (m, 5H)

EXAMPLE 5

Synthesis of (5S)-5-(4-but-3-enyloxy-3,5-dimethoxy-phenyl)-5,9-dihydro-8H-furo [3',4':6,7]naphtho[2,3-d][1,3]dioxol-6-one (Compound 1-7)

To a stirred solution of 4'-demethyl-β-apopicropodophyllin (300 mg, 0.78 mmol) in anhydrous N,N-dimethylformamide (2 mL) was added sodium hydride (40 mg, 60%, 1.0 mmol) at below 0° C. After the mixture was stirred at same temperature for 1 hr, cyclopropylmethyl trifluorosulfonate (210 mg, 1.02 mmol)(reference of preparation, Journal of medicinal chemistry, 2015, vol. 58, pp 6151-6178) was added dropwise to the mixture. The reaction mixture was stirred for 1 hr, quenched with water (20 mL) and extracted with ethyl acetate (2×10 mL). The combined organic layer was washed twice with water (5 mL), dried over MgSO$_4$ and concentrated in vacuo. The concentrate was purified by column chromatography on silica gel (ethyl acetate/n-hexane:1/3) to afford 49 mg (14%) of the desired product.

NMR(CDCl$_3$) δ (ppm): 6.72 (s, 1H), 6.63 (s, 1H), 6.36 (s, 2H), 5.95 (d, J=1.7 Hz, 2H), 5.93-5.82 (m, 2H), 5.11 (d, J=17.2 Hz, 1H), 5.03 (d, J=10.2 Hz, 1H), 4.91-4.76 (m, 3H), 3.96 (t, J=7.1 Hz, 2H), 3.91-3.64 (m, 2H), 3.76 (s, 6H), 2.51-2.46 (m, 2H)

EXAMPLE 6

Synthesis of (5S)-5-[3,5-dimethoxy-4-(4-fluorobenzyloxy)-phenyl]-5,9-dihydro-8H-furo[3',4':6,7]naphtho[2,3-d][1,3]dioxol-6-one (Compound 1-15)

To a stirred solution of 4'-demethyl-β-apopicropodophyllin (200 mg, 0.52 mmol) in anhydrous N,N-dimethylformamide (5 mL) was added sodium hydride (25 mg, 60%, 0.62 mmol) at below 0° C. After the mixture was stirred at same temperature for 1 hr, 4-fluorobenzyl bromide (147 mg, 0.78 mmol) was added dropwise to the mixture. The reaction mixture was stirred at room temperature for 2 hrs, quenched with water (30 mL) and extracted with ethyl acetate (2×20 mL). The combined organic layer was washed twice with water (10 mL), dried over MgSO$_4$ and concentrated in vacuo. The concentrate was purified by column chromatography on silica gel (ethyl acetate/n-hexane:1/2) to afford 79 mg (30%) of the desired product.

NMR (DMSO) δ (ppm): 7.44 (dd, J=8.6, 5.7 Hz, 2H), 7.17 (t, J=8.9 Hz, 2H), 6.88 (s, 1H), 6.81 (s, 1H), 6.48 (s, 2H), 5.99 (s, 1H), 5.94 (s, 1H), 5.04 (dd, J=48.2, 17.4 Hz, 2H), 4.79 (s, 2H), 4.77 (s, 1H) 4.02-3.94 (m, 1H), 3.78-3.67 (m, 1H), 3.69 (s, 6H)

EXAMPLE 7

Synthesis of (5S)-5-[3,5-dimetoxy-4-(4-trifluoromethyl-benzyloxy)-phenyl]-5,9-dihydro-8H-furo[3',4':6,7]naphtho[2,3-d][1,3]dioxol-6-one (Compound 1-13)

To a stirred solution of 4'-demethyl-β-apopicropodophyllin (200 mg, 0.52 mmol) in anhydrous N,N-dimethylformamide (2 mL) was added sodium hydride (25 mg, 60%, 0.62 mmol) at below 0° C. After the mixture was stirred at same temperature for 1 hr, 4-fluoromethylbenzyl bromide (180 mg, 0.78 mmol) was added dropwise to the mixture. The reaction mixture was stirred at room temperature for 2 hr, quenched with water (20 mL) and extracted with ethyl acetate (2×20 mL). The combined organic layer was washed twice with water (10 mL), dried over MgSO$_4$ and concentrated in vacuo. The concentrate was purified by column chromatography on silica gel (ethyl acetate/n-hexane:1/2) to afford 157 mg (55%) of the desired product.

NMR (DMSO) δ (ppm): 7.72 (d, J=8.3 Hz, 2H), 7.66 (d, J=8.2 Hz, 2H), 6.88 (s, 1H), 6.81 (s, 1H), 6.50 (s, 2H), 5.99 (s, 1H), 5.94 (s, 1H), 5.10 (d, J=17.3 Hz, 1H), 4.98 (d, J=17.1 Hz, 1H), 4.93 (s, 2H), 4.78 (s, 1H) 3.99 (dd, J=22.3, 3.7 Hz, 1H), 3.78-3.63 (m, 1H), 3.70 (s, 6H)

EXAMPLE 8

Synthesis of (5S)-5-[3,5-dihydroxy-4-(4-methyl-benzyloxy)-phenyl]-5,9-dihydro-8H-furo[3',4':6,7] naphtho[2,3-d][1,3]dioxol-6-one (Compound 1-14)

To a stirred solution of 4'-demethyl-β-apopicropodophyllin (200 mg, 0.52 mmol) in anhydrous N,N-dimethylformamide (2 mL) was added sodium hydride (25 mg, 60%, 0.62 mmol) at below 0° C. After the mixture was stirred at same temperature for 1 hr, 4-methylbenzyl bromide (140 mg, 0.78 mmol) was added dropwise to the mixture. The reaction mixture was stirred at room temperature for 2 hrs, quenched with water (20 mL) and extracted with ethyl acetate (2×10 mL). The combined organic layer was washed twice with water (10 mL), dried over $MgSO_4$ and concentrated in vacuo. The concentrate was purified by column chromatography on silica gel (ethyl acetate/n-hexane:1/2) to afford 157 mg (55%) of the desired product.

NMR (DMSO) δ (ppm): 7.31 (d, J=7.9 Hz, 2H), 7.15 (d, J=7.9 Hz, 2H), 6.88 (s, 1H), 6.81 (s, 1H), 6.48 (s, 2H), 5.99 (s, 1H), 5.94 (s, 1H), 5.10 (d, J=17.3 Hz, 1H), 4.98 (d, J=17.5 Hz, 1H), 4.76 (s, 2H), 3.99 (dd, J=22.1, 4.2 Hz, 1H), 3.76-3.73 (m, 1H), 3.71 (s, 6H), 2.29 (s, 3H)

[Anti-Cancer Effect in Cancer Cell Line]

1) Cell Culture

Human lung cancer cells A549, NCl-H460 and 7 cancer cell lines were cultured in RPMI 1640 medium containing 10% FBS (Gibco, USA) and 1% penicillin-streptomycin. Human colon cancer cell HCT-116 cell line was cultured in McCoy's 5A medium containing 10% FBS (Gibco, USA) and 1% penicillin-streptomycin. Human leukemia cancer cell HL-60 cell line was cultured in IMDM medium containing 20% FBS (Gibco, USA) and 1% penicillin-streptomycin. Human normal cell line WI-38 was cultured in MEM containing 10% FBS (Gibco, USA), 1% penicillin-streptomycin, and 1% Non-Essential Amin Acids solution. Human normal cell line HUVEC cultured in Human Endothelial Growth Medium containing. All the cells were cultured in sterilized cell culture plastic dishes or 96-well plastic plates in a humidified incubator filled with 95% air and 5% $CO_2$ gas and maintained at a temperature of 37° C.

2) Test Method

First, the cells are seeded in a 96-well plate (Nunc, 165305) at a volume of 100 μl, and then cultured in an incubator overnight to confirm that they grow well on the plate. Depending on the concentration of the drugs, each well is treated with 100 μl of the compound and then incubated to allow cells and compounds to react for 48 hrs. PrestoBlue Cell Viability Reagent (Invitrogen, A13262) was added to the compound-treated well, and then the plates were incubated in a humidified incubator at 37° C. for 30 mins. Each well was measured at a fluorescence detected with the wavelength of an excitation of 560 nm and an emission of 590 nm using by microplate reader (BioTek, Synergy H1). The $IC_{50}$ value is calculated by using the Gen5 software.

The $IC_{50}$ value of the compound in the present invention and positive control Etoposide describe in Table 3 and 4.

TABLE 3

IC50 values for 48 h (unit; μM)

| | cell line | Etoposide | example 1 | example 2 | example 3 | example 4 |
|---|---|---|---|---|---|---|
| lung | A549 | 2.159 | 0.065 | 0.202 | 0.127 | 0.698 |
| | H460 | 0.971 | 0.06 | 0.134 | 0.174 | 0.796 |
| | H1299 | 40.12 | >50 | >50 | >50 | — |
| | H1650 | >50 | >50 | >50 | >50 | — |
| | H1975 | >50 | >50 | >50 | >50 | — |
| | HCC827 | >50 | >50 | >50 | >50 | — |
| | H146 | >50 | >50 | >50 | >50 | — |
| breast | MCF-7 | >50 | >50 | >50 | >50 | — |
| | MDA-MB-231 | >50 | >50 | >50 | >50 | >50 |
| colon | HCF116 | 7.289 | 0.129 | 1.392 | 0.234 | 1.57 |
| leukemia | HL-60 | 2.43 | 0.03 | 0.25 | 0.181 | >50 |
| | K562 | — | >50 | >50 | >50 | 0.398 |
| pancreas | CFPAC-1 | 42.02 | >50 | >50 | >50 | — |
| | BxPC-3 | >50 | >50 | >50 | >50 | — |
| normal | WI-38 | >50 | >50 | >50 | >50 | >50 |
| | WI-26 | — | >50 | >50 | >50 | — |
| | HUVEC | >50 | >50 | >50 | >50 | >50 |

TABLE 4

IC50 values for 48 h(unit; μM)

| | cell line | Etoposide | example 5 | example 6 | example 7 | example 8 |
|---|---|---|---|---|---|---|
| lung | A549 | 2.159 | >50 | 0.288 | >50 | >50 |
| | H460 | 0.971 | >50 | 0.437 | >50 | >50 |
| | H1299 | 40.12 | — | — | — | — |
| | H1650 | >50 | — | — | — | — |
| | H1975 | >50 | — | — | — | — |
| | HCC827 | >50 | — | — | — | — |
| | H146 | >50 | — | — | — | — |
| breast | MCF-7 | >50 | — | — | — | — |
| | MDA-MB-231 | >50 | >50 | >50 | >50 | >50 |
| colon | HCF116 | 7.289 | >50 | >50 | >50 | >50 |
| leukemia | HL-60 | 2.43 | >50 | >50 | >50 | >50 |
| | K562 | — | — | 0.247 | — | — |
| pancreas | CFPAC-1 | 42.02 | — | — | — | — |
| | BxPC-3 | >50 | — | — | — | — |
| normal | WI-38 | >50 | >50 | >50 | >50 | >50 |
| | WI-26 | — | — | — | — | — |
| | HUVEC | >50 | >50 | >50 | >50 | >50 |

3) Anticancer Efficacy Against Lung Cancer

Among the lung cancer cell lines listed in Tables 3 and 4, A549 and H460 are non-small cell lung cancer cell lines, which clinically show the highest case fatality rates in Korea. The compounds prepared according to Examples 1 to 4 and Example 6 of the present invention exhibited particularly excellent cytotoxicity against the A549 and H460 cell lines, and showed 10 to 200-fold stronger anticancer efficacy, compared with the reference drug, etoposide.

On the other hand, the compounds of Examples 5, 7 and 8 had $IC_{50}$ values of 50 μM or more for the A549 and H460 cell lines, indicating similar anticancer efficacy to that of the reference drug. In addition, compared with the other lung cancer cell lines, except the A549 and H460 cell lines, the compounds of Examples 1 to 3 exhibited almost similar anticancer efficacy to that of etoposide.

4) Anticancer Efficacy Against Colorectal Cancer and Blood Cancer

The compounds of Examples 1 to 4 exhibited excellent anticancer efficacy against the colorectal cancer cell line HCT-116, and the compounds of Examples 1 to 3 exhibited excellent anticancer efficacy against the blood cancer cell line HL-60. Specifically, the $IC_{50}$ values of the compounds of Examples 1 to 4 are 0.011 to 1.57 μM for the HCT-116 cell line, indicating that these compounds exhibited very excellent anticancer efficacy, which is 660-fold higher than that of the reference drug.

In addition, the $IC_{50}$ values of the compounds of Examples 1 to 3 are 0.004 to 0.25 μM for the HL-60 cell line, indicating that these compounds exhibited 10 to 600-fold stronger anti-cancer efficacy than the reference drug. However, the compounds of Examples 4 and 6 exhibited particularly excellent effects against the blood cancer cell line K562.

5) Anticancer Efficacy Against Breast Cancer and Pancreatic Cancer

All of the compounds of Examples 1 to 8 had $IC_{50}$ values of 50 μM or more for the breast cancer cell lines, MCF-7 and MDA-MB-231 cell lines, indicating that these compounds exhibited similar anticancer efficacy to that of the reference drug. In addition, for the pancreatic cell lines, CFPAC-1 and BxCP-3 cell lines, the compounds of Examples 1 to 3 exhibited similar anti-cancer efficacy to that of the reference drug. For reference, the compounds of Examples 4 to 8 were not tested for toxicity against a pancreatic cancer cell line.

6) Toxicity Test Against Normal Cells

In the results of the toxicity test against normal human cells, that is, WI-38, WI-26 and HUVEC cell lines, it was confirmed that all of the $IC_{50}$ values of the compounds of Examples 1 to 8 are 50 μM or more. Therefore, since the compounds of Examples 1 to 8 have almost no toxicity against normal human cells, it was confirmed that the risk of side effects is very low when used as an anticancer agent.

7) Comprehensive Evaluation

From the above-described cytotoxicity test results, it was confirmed that the compounds prepared according to Examples of the present invention have significant anticancer efficacy against, particularly, lung cancer, colorectal cancer and blood cancer, and further, when used as an anticancer agent, it was shown that the risk of side effects is very low.

The invention claimed is:
1. A compound represented by Formula 1 below or a pharmaceutically acceptable salt thereof:

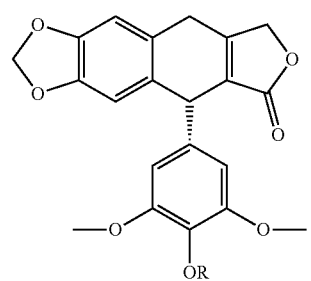

[Formula 1]

In Formula 1, R is a $C_2$ to $C_{10}$ alkyl group containing an allyl- or alkyne, a —[CH$_2$]$_n$—$C_3$ to $C_8$ cycloalkyl group, a substituted or unsubstituted —[CH$_2$]$_n$-phenyl group, a substituted or unsubstituted —[CH$_2$]$_n$—$C_5$ to $C_6$ heteroaromatic group, a —C(=O)—$C_1$ to $C_8$ alkyl group, a substituted or unsubstituted —C(=O)—[CH$_2$]$_n$-phenyl group, or a substituted or unsubstituted —C(=O)—[CH$_2$]$_n$—$C_5$ to $C_6$ heteroaromatic group, wherein n is an integer of 0 to 6.

2. The compound of claim 1, wherein the compound is selected from the group consisting of:
acetic acid (5S)-2,6-dimethoxy-4-(6-oxo-5,6,8,9-tetrahydrofuro[3',4':6,7]naphtho[2,3-d] [1,3]dioxol-5-yl)-phenyl ester;
benzoic acid (5S)-2,6-dimethoxy-4-(6-oxo-5,6,8,9-tetrahydrofuro[3',4':6,7]naphtho[2,3-d][1,3]dioxol-5-yl)-phenyl ester;
propionic acid (5S)-2,6-dimethoxy-4-(6-oxo-5,6,8,9-tetrahydrofuro[3',4':6,7]naphtho [2,3-d] [1,3]dioxol-5-yl)-phenyl ester;
nicotinic acid (5S)-2,6-dimethoxy-4-(6-oxo-5,6,8,9-tetrahydrofuro[3',4':6,7]naphtho[2,3-d][1,3]dioxol-5-yl)-phenyl ester;
1 H-pyrrole-2-carboxylic acid (5S)-2,6-dimethoxy-4-(6-oxo-5,6,8,9-tetrahydrofuro [3',4':6,7]naphtho[2,3-d][1, 3]dioxol-5-yl)-phenyl ester;
3H-imidazole-4-carboxylic acid (5S)-2,6-dimethoxy-4-(6-oxo-5,6,8,9-tetrahydrofuro [3',4':6,7]naphtho[2,3-d] [1,3]dioxol-5-yl)-phenyl ester;
(5S)-5-(4-but-3-enyloxy-3,5-dimethoxy-phenyl)-5,9-dihydro-8H-furo[3',4':6,7]naphtho [2,3-d][1,3]dioxol-6-one;
(5S)-5-(4-cyclohexylmethoxy-3,5-dimethoxy-phenyl)-5, 9-dihydro-8H-furo[3',4':6,7] naphtho [2,3-d][1,3]dioxol-6-one;
(5S)-5-(4-cyclopentylmethoxy-3,5-dimethoxy-phenyl)-5, 9-dihydro-8H-furo[3',4':6,7] naphtho[2,3-d][1,3]dioxol-6-one;
(5S)-5-[4-(2-cyclohexyl-ethoxy)-3,5-dimethoxy-phenyl]-5,9-dihydro-8 H-furo[3',4':6,7] naphtho[2,3-d][1,3]dioxol-6-one;
(5S)-5-[3,5-dimethoxy-4-(pyridin-4-ylmethoxy)-phenyl]-5,9-dihydro-8H-furo[3',4':6,7] naphtho[2,3-d][1,3]dioxol-6-one;
(5S)-5-(4-benzyloxy-3,5-dimethoxy-phenyl)-5,9-dihydro-8H-furo[3',4':6,7]naphtho[2,3-d][1,3]dioxol-6-one;
(5S)-5-[3,5-dimethoxy-4-(4-trifluoromethyl-benzyloxy)-phenyl]-5,9-dihydro-8H-furo [3',4':6,7]naphtho[2,3-d] [1,3]dioxol-6-one;
(5S)-5-[3,5-dimethoxy-4-(4-methyl-benzyloxy)-phenyl]-5,9-dihydro-8H-furo[3',4':6,7] naphtho[2,3-d][1,3]dioxol-6-one; and (5S)-5-[3,5-dimethoxy-4-(4-fluorobenzyloxy)-phenyl]-5,9-dihydro-8H-furo[3',4':6,7] naphtho[2,3-d][1,3]dioxol-6-one.

3. A pharmaceutical composition for treating cancer, comprising the compound represented by Formula 1 of claim 1 or a pharmaceutically acceptable salt thereof as an active ingredient.

* * * * *